(12) United States Patent
Huang

(10) Patent No.: US 12,128,198 B2
(45) Date of Patent: Oct. 29, 2024

(54) GUIDE WIRE FRICTION FEEDBACK DEVICE AND METHOD FOR INTERVENTIONAL SURGICAL ROBOT

(71) Applicant: BEIJING WEMED MEDICAL EQUIPMENT CO., LTD., Beijing (CN)

(72) Inventor: Tao Huang, Beijing (CN)

( * ) Notice: Subject to any disclaimer, the term of this patent is extended or adjusted under 35 U.S.C. 154(b) by 583 days.

(21) Appl. No.: 17/210,502

(22) Filed: Mar. 24, 2021

(65) Prior Publication Data

US 2022/0226619 A1 Jul. 21, 2022

Related U.S. Application Data

(63) Continuation of application No. PCT/CN2021/073716, filed on Jan. 26, 2021.

(30) Foreign Application Priority Data

Oct. 29, 2020 (CN) .......................... 202011181462.X

(51) Int. Cl.
*A61M 25/09* (2006.01)
*A61B 34/30* (2016.01)
(Continued)

(52) U.S. Cl.
CPC ....... *A61M 25/09041* (2013.01); *A61B 34/30* (2016.02); *A61B 90/10* (2016.02);
(Continued)

(58) Field of Classification Search
CPC ............ A61M 25/09041; A61M 25/01; A61M 25/0102; A61M 25/0105; A61M 25/0127;
(Continued)

(56) References Cited

U.S. PATENT DOCUMENTS 5,742,389 A * 4/1998 Zavislan .................. G01J 3/02
356/326

FOREIGN PATENT DOCUMENTS

| CN | 110236680 A | * | 9/2019 | |
| CN | 110269998 A | * | 9/2019 | ........ A61M 25/0116 |
| CN | 110882060 A | * | 3/2020 | |

OTHER PUBLICATIONS

Dong et al., Chinese Patent Document CN110882060A, translation from Espacenet (Year: 2020).*

(Continued)

*Primary Examiner* — Matthew Kremer
*Assistant Examiner* — Jonathan Drew Moroneso

(57) ABSTRACT

The disclosure relates to a guide wire friction feedback device and method for interventional surgical robot. The friction feedback device includes two sets of driving end parts, driven end parts and clamping parts symmetrically arranged along the guide wire. The structure of the friction feedback device is relatively simple, compact and stable. When the clamping part is subjected to the force in the clamping direction of the guide wire, the force is transmitted to the right-angle connecting plate through the U-shaped slot connector, the first slider and the first micro linear guide. The high precision load cell only measures the axial force of the guide wire, that is, the push-pull force felt by the high precision load cell (that is, the friction on the guide wire), so as to judge the force change of the axial friction of the guide wire.

4 Claims, 4 Drawing Sheets

(51) Int. Cl.
  *A61B 90/10* (2016.01)
  *A61B 90/00* (2016.01)
  *A61B 90/11* (2016.01)
  *A61B 90/25* (2016.01)
  *A61M 25/01* (2006.01)

(52) U.S. Cl.
  CPC ... *A61B 2034/301* (2016.02); *A61B 2034/302* (2016.02); *A61B 2034/303* (2016.02); *A61B 90/11* (2016.02); *A61B 90/25* (2016.02); *A61M 25/01* (2013.01); *A61M 25/0102* (2013.01); *A61M 25/0105* (2013.01); *A61M 25/0127* (2013.01); *A61M 25/013* (2013.01)

(58) Field of Classification Search
  CPC ..... A61M 25/013; A61M 25/09; A61B 34/30; A61B 90/10; A61B 90/11; A61B 90/25; A61B 2034/301; A61B 2034/302; A61B 2034/303; A61B 90/06; A61B 2090/064
  See application file for complete search history.

(56) References Cited

OTHER PUBLICATIONS

Chen et al., Chinese Patent Document CN110269998A, translation from Clarivate Analytics (Year: 2019).*
Huang, Chinese Patent Document CN110236680A, translation from Clarivate Analytics (Year: 2019).*

* cited by examiner

GUIDE WIRE FRICTION FEEDBACK DEVICE AND METHOD FOR INTERVENTIONAL SURGICAL ROBOT

CROSS-REFERENCE TO RELATED APPLICATIONS

This application is a continuation of International Patent Application No. PCT/CN2021/073716 with a filing date of Jan. 26, 2021, designating the United States, now pending, and further claims priority to Chinese Patent Application No. 202011181462.X with a filing date of Oct. 29, 2020. The content of the aforementioned applications, including any intervening amendments thereto, are incorporated herein by reference.

TECHNICAL FIELD

The present disclosure relates to the field of minimally invasive vascular technology, and more specifically, to a guide wire friction feedback device and method for interventional surgical robot.

BACKGROUND

Minimally invasive interventional therapy is the main treatment for cardiovascular and cerebrovascular diseases. Compared with traditional surgery, it has the advantages of small incision and short postoperative recovery time.

Cardiovascular and cerebrovascular interventional surgery is a process in which the doctor manually sends catheter, guide wire and stent into the body of patient to complete the treatment.

Interventional surgery has the following problems. In an operation process, because DSA will send out X-rays, the physical strength of doctors declines rapidly, and the attention and stability also decline, which leads to the decline of operation accuracy. It is easy to cause accidents such as vascular intima damage, vascular perforation and rupture caused by improper pushing force, which endangers the lives of patients. Secondly, the cumulative damage of long-term ionizing radiation greatly increases the risk of leukemia, cancer and acute cataract of doctors. The phenomenon that doctors accumulate rays continuously because of interventional operation has become a problem that cannot be ignored because it damages the professional life of doctors and restricts the development of the interventional operation.

With the help of robot technology, the above problems can be effectively solved. The accuracy and stability of surgical operation can also be greatly improved. At the same time, the injury of radiation to interventional doctors can be effectively reduced and the probability of intraoperative accidents can be reduced. Therefore, more and more attention has been paid to the auxiliary robot of cardiovascular and cerebrovascular interventional surgery, and it has gradually become a key research and development object in the field of medical robot in scientific and technological powers. However, it is widely known that the robot does not feel, and how to ensure safety in surgery is a problem that people have been concerned about. How to make the robot feel like a doctor and feel the danger in time is a key problem to be considered.

In China, there are several problems in the force feedback detection of the guide wire of interventional surgical robot: (1) the structure is relatively bulky and complex, and the force feedback detection device of the guide wire leads to inconvenient installation and replacement of the guide wire on the robot; (2) the direct sensor is used to measure the force change of the guide wire, which can not effectively guarantee the sterile environment; (3) there is no good method to indirectly measure the axial friction of guide wire (4) the clamping force of guide wire has great interference on the measurement of guide wire friction, which makes it difficult to measure the friction.

Therefore, how to provide a guide wire friction feedback device for interventional surgical robot is an urgent problem for those skilled in the art.

SUMMARY

The present disclosure aims to solve one of the above technical problems in the prior art at least to a certain extent.

Therefore, an object of the disclosure is to provide a guide wire friction feedback device for interventional surgical robot. The device solves the problem that the structure is relatively bulky and complex in the prior art, and the force feedback detection device of the guide wire leads to inconvenient installation and replacement of the guide wire on the robot. The device is an indirect measurement device.

The guide wire friction feedback device for interventional surgical robot provided by the present disclosure includes two sets of driving end parts, driven end parts and clamping parts symmetrically arranged along the guide wire.

Each set of the driving end part includes a U-shaped slot connector, a high precision load cell, a first slider, a first micro linear guide, a right-angle connecting plate and a driving end connecting piece. A top of the driving end connecting piece slides along a direction parallel to the guide wire on a length direction of a rectangular bottom plate driving the driving end of mechanism. A bottom of the right-angle connecting plate slides perpendicularly to the direction of the guide wire on the top of the driving end connecting piece. An outside of a vertical plate connected on one end of the right-angle connecting plate is butted with a camshaft, and the top of the other end is fixed with the first micro linear guide parallel to the direction of the guide wire. The first slider slides on the first micro linear guide, and the U-shaped slot connector is fixed on the top of the first slider to counteract a clamping force of the guide wire. The high precision load cell is arranged perpendicularly to the guide wire. One end of the high precision load cell is fixed on the inner side of the vertical plate, and the other end is inserted into a notch of the U-shaped slot connector, and the width of the notch is greater than the width of the high precision load cell. The high precision load cell is used to measure the friction on the guide wire. A side far away from the notch of the U-shaped slot connector is fixed with one end of a first clamping part.

Each set of the driven end part includes a second clamp part arranged corresponding to the first clamp part, and a driven end connecting piece arranged corresponding to the driving end connecting piece, for clamping and pushing the guide wire.

According to the above technical solution, compared with the prior art, the present disclosure provides a guide wire friction feedback device for interventional surgical robot, with relatively simple, compact structure and good stability. When the clamping part is subjected to the force in the clamping direction of the guide wire, the force is transmitted to the right-angle connecting plate through the U-shaped slot connector, the first slider and the first micro linear guide. The high precision load cell only measures the axial force of the guide wire, that is, the push-pull force felt by the high precision load cell (that is, the friction on the guide wire), so as to judge the force change of the axial friction of the guide wire. It gives timely operation reminder to doctors and protect the safety of patients. The disclosure adopts an indirect force measuring method, and solves the problem of inconvenient installation of guide wire and force measuring device.

Further, each set of the driving end part includes a second slider and a second micro linear guide. The bottom of the right-angle connecting plate is fixed with the second slider along a vertical direction with the guide wire, and the top of the driving end connecting piece is provided with the second micro linear guide sliding with the second slider.

Further, each set of the driving end part includes a spring and a polytetrafluoro patch. Two ends of the spring are respectively hooked and fixed between the outer side of the vertical plate and the polytetrafluoro patch. The polytetrafluoro patch is always butted with the camshaft.

Further, each set of the driven end part includes a third slider, a driven end connecting plate, and a third micro linear guide. The driven end connecting plate is arranged opposite to the right-angle connecting plate. The driven end connecting piece is fixed near the side of the guide wire on the driven end connecting plate. The top of the driven end connecting plate is fixed with the third micro linear guide in parallel with the guide wire. The second clamping part is fixed on the top of the third slider and slides on the third micro linear guide.

Further, each set of the first clamping part includes a first cylindrical electromagnet and an active movable block. The axis of the first cylindrical electromagnet is perpendicular to the direction of the guide wire, and one end of the first cylindrical electromagnet is fixed on the U-shaped slot connector, and the other end is magnetically connected with the active movable block.

Further, each set of the second clamping part includes a second cylindrical electromagnet and a passive movable block. The second cylindrical electromagnet is vertically fixed on the top of the third slider. The plane of the axis of the second cylindrical electromagnet is parallel to the plane of the guide wire. The top of the second cylindrical electromagnet is magnetically connected with the passive movable block rubbing with the active movable block.

The present disclosure provides a guide wire friction feedback method for interventional surgical robot. The method includes: using the above guide wire friction feedback device for interventional surgical robot in conjunction with a reciprocating motion device of the interventional surgery robot;

lamping alternately and moving, by two sets of the clamping parts, the guide wire during the reciprocating motion of the guide wire;

measuring the friction force in a motion of the guide wire by detecting a force change signal from the high precision load cell to indirectly reflect the force on a guide wire end; and transmitting a data to a control end of driving end of the robot propulsion mechanism to give timely feedback to a doctor.

Therefrom, the disclosure adopts the indirect force measuring method, and solves the problem that the guide wire and the force measuring device are not convenient to install.

BRIEF DESCRIPTION OF THE DRAWINGS

In order to explain the embodiments of the present disclosure or the technical solutions in the prior art more clearly, the following drawings that need to be used in the description of the embodiments or the prior art will be briefly introduced. Obviously, the drawings in the following description are only embodiments of the present disclosure. For those of ordinary skill in the art, other drawings can be obtained based on the drawings disclosed without creative work.

Figure 1:
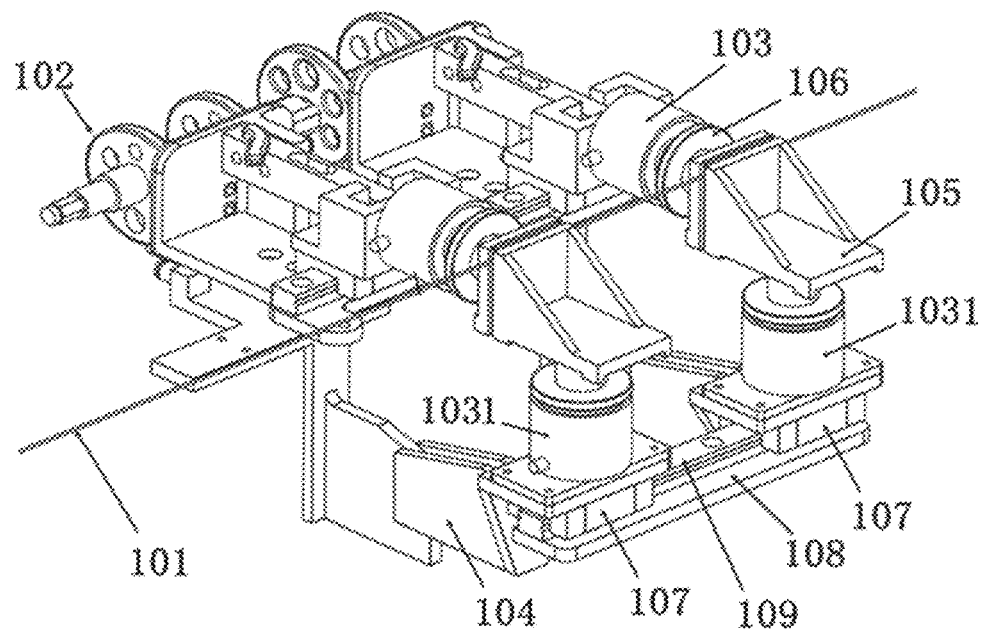
FIG. 1 is a three-dimensional diagram of the guide wire friction feedback device for interventional surgical robot provided by the disclosure.

where, guide wire (101), camshaft (102), first cylindrical electromagnet (103), second cylindrical electromagnet (1031), driven end connecting piece (104), passive movable block (105), active movable block (106), third slider (107), driven end connecting plate (108), third micro linear guide (109), U-shaped slot connector (201), high precision load cell (202), first slider (203), first micro linear guide (204), right-angle connecting plate (205), second slider (206), second micro linear guide (207), polytetrafluoro patch (208), driving end connecting piece (209), gear transmission group (300), rectangular bottom plate (D).

DETAILED DESCRIPTION OF EMBODIMENTS

Hereinafter, embodiments of the present disclosure will be described in detail, embodiments of which are shown in the accompanying drawings, in which the same or similar elements or elements having the similar or similar functions are denoted by the same reference numerals throughout. The embodiments described below by reference to the accompanying drawings are exemplary and intended to explain the disclosure and should not be construed as limiting the disclosure.

In the description of the disclosure, it is to be understood that, the terms "up", "down", "front", "back", "left", "right", "vertical", "horizontal", "top", "bottom", "inside", "outside" etc., the orientation or positional relationship indicated is based on the shown in the drawings, merely to facilitate the description of the disclosure and to simplify the description, rather than indicating or implying that the devices or elements referred to must have a particular orientation, be constructed and operate in a specific orientation, and therefore it should not be construed as limiting the disclosure.

In addition, the term "first," "second" are used for descriptive purpose only and are not to be construed as indicating or implying relative importance or implicitly indicate the number of technical features indicated. Thus, a feature defined as "first" or "second" may include one or more of the features, either explicitly or implicitly. In the description of the present disclosure, "plural" means two or more than two, unless otherwise specifically defined.

In the present disclosure, unless otherwise expressly specified and defined, the terms "install," "connect," and "fix" are to be understood in a broad sense. For example, a fixed connection or a detachable connection, or in one piece; either mechanically or electrically connected; either directly or indirectly connected through an intermediate medium, either in communication between the two elements or in an interactive relationship between them. The specific meanings of the above terms in the present disclosure may be understood by those of ordinary skill in the art as the case may be.

In the present disclosure, unless otherwise expressly specified and defined, the first feature is "up" or "down" to the second feature may comprise the first and second features in direct contact; it is also possible to include the first and second features not in direct contact but by means of a further feature contact between them. In addition, that word "up", "above" and "on" of the first feature include the first feature being directly above and obliquely above the second feature, or simply indicate that the level of the first feature is higher than that of the second feature. If the first feature is "down", "below" and "under" the second feature includes the first feature being directly below and diagonally below the second feature, or simply indicating that the height of the first feature is less than the second feature.

Referring to FIG. 1, the present disclosure provides a guide wire friction feedback device for interventional surgical robot, including two sets of driving end parts, driven end parts and clamping parts symmetrically arranged along the guide wire 101.

Each set of the driving end part includes a U-shaped slot connector 201, a high precision load cell 202, a first slider 203, a first micro linear guide 204, a right-angle connecting plate 205 and a driving end connecting piece 209. A top of the driving end connecting piece 209 slides along a direction parallel to the guide wire 101 on a length direction of a rectangular bottom plate D driving the driving end of mechanism. A bottom of the right-angle connecting plate 205 slides perpendicularly to the direction of the guide wire 101 on the top of the driving end connecting piece 209. An outside of a vertical plate connected on one end of the right-angle connecting plate 205 is butted with a camshaft 102, and the top of the other end is fixed with the first micro linear guide 204 parallel to the direction of the guide wire 101. The first slider 203 slides on the first micro linear guide 204, and the U-shaped slot connector 201 is fixed on the top of the first slider 203 to counteract a clamping force of the guide wire 101. The high precision load cell 202 is arranged perpendicularly to the guide wire 101. One end of the high precision load cell 202 is fixed on the inner side of the vertical plate, and the other end is inserted into a notch of the U-shaped slot connector 201, and the width of the notch is greater than the width of the high precision load cell 202. The high precision load cell 202 is used to measure the friction on the guide wire 101. A side far away from the notch of the U-shaped slot connector 201 is fixed with one end of a first clamping part.

Each set of the driven end part includes a second clamp part arranged corresponding to the first clamp part, and a driven end connecting piece 104 arranged corresponding to the driving end connecting piece 209, for clamping and pushing the guide wire 101.

The present disclosure provides a guide wire friction feedback device for interventional surgical robot, with relatively simple, compact structure and good stability. When the clamping part is subjected to the force in the clamping direction of the guide wire, the force is transmitted to the right-angle connecting plate through the U-shaped slot connector, the first slider and the first micro linear guide. The high precision load cell only measures the axial force of the guide wire, that is, the push-pull force felt by the high precision load cell (that is, the friction on the guide wire), so as to judge the force change of the axial friction of the guide wire. It gives timely operation reminder to doctors and protect the safety of patients. The disclosure adopts an indirect force measuring method, and solves the problem of inconvenient installation of guide wire and force measuring device.

Figure 2:
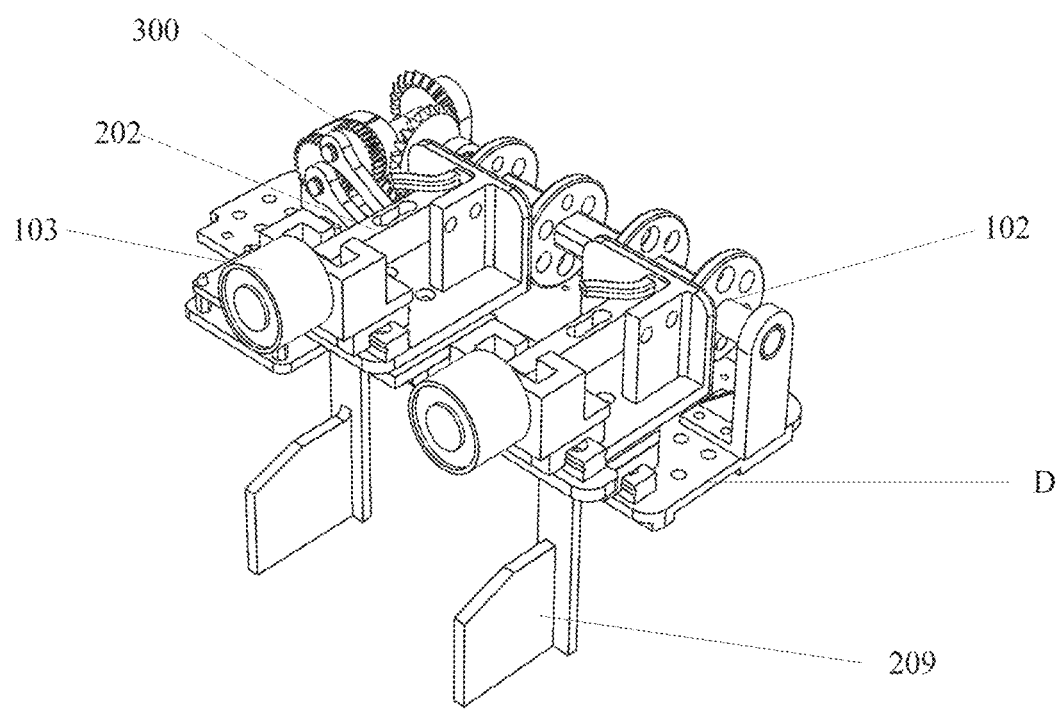
FIG. 2 is a stereoscopic view of the driving end part of the guide wire friction feedback device for interventional surgical robot provided by the disclosure.
Figure 3:
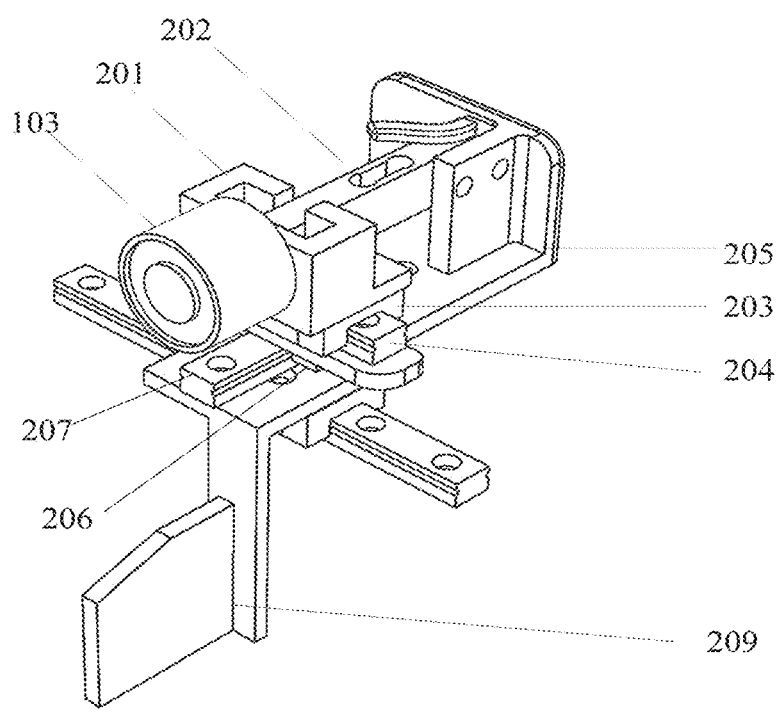
FIG. 3 is a partial schematic diagram of FIG. 2.

Referring to FIG. 2 and FIG. 3, each set of the driving end part further includes a second slider 206 and a second micro linear guide 207. The bottom of the right-angle connecting plate 205 is fixed with the second slider 206 along a vertical direction with the guide wire 101, and the top of the driving end connecting piece 209 is provided with the second micro linear guide 207 sliding with the second slider 206.

Advantageously, each set of the driving end part further includes a spring and a polytetrafluoro patch 208. Two ends of the spring are respectively hooked and fixed between the outer side of the vertical plate and the polytetrafluoro patch (206). The polytetrafluoro patch (208) is always butted with the camshaft (102).

Figure 4:
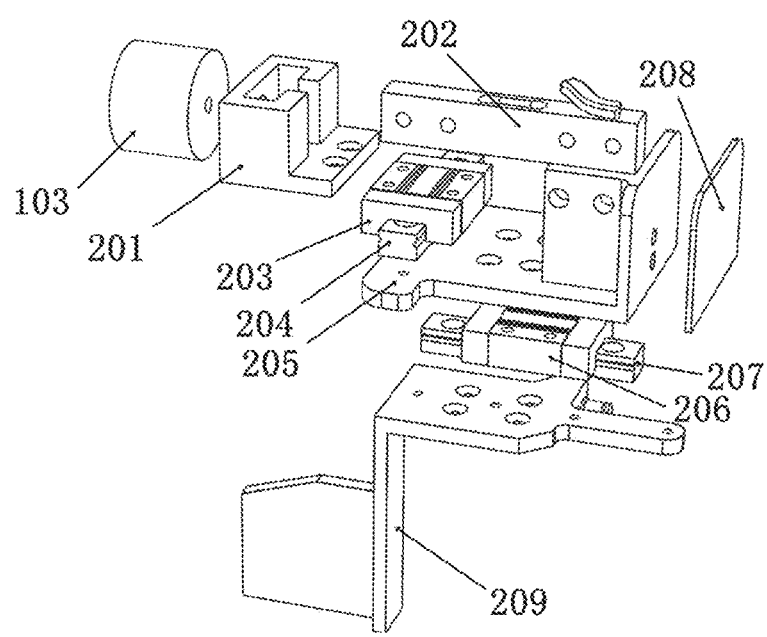
FIG. 4 is an explosion diagram of the guide wire friction feedback device for interventional surgical robot provided by the disclosure.

Referring to FIG. 4, each set of the driven end part further includes a third slider 107, a driven end connecting plate 108, and a third micro linear guide 109. The driven end connecting plate 108 is arranged opposite to the right-angle connecting plate 205. The driven end connecting piece 104 is fixed near the side of the guide wire 101 on the driven end connecting plate 108. The top of the driven end connecting plate 108 is fixed with the third micro linear guide 109 in parallel with the guide wire 101. The second clamping part is fixed on the top of the third slider 107 and slides on the third micro linear guide 109.

Referring to FIG. 1 and FIG. 2, each set of the first clamping part includes a first cylindrical electromagnet 103 and an active movable block 106. The axis of the first cylindrical electromagnet 103 is perpendicular to the direction of the guide wire 101. One end of the first cylindrical electromagnet 103 is fixed on the U-shaped slot connector 201, and the other end is magnetically connected with the active movable block 106.

Referring to FIG. 4, each set of the second clamping part includes a second cylindrical electromagnet 1031 and a passive movable block 105. The second cylindrical electromagnet 1031 is vertically fixed on the top of the third slider 107. The plane of the axis of the second cylindrical electromagnet 1031 is parallel to the plane of the guide wire 101, and the top of the second cylindrical electromagnet 1031 is magnetically connected with the passive movable block 105 rubbing with the active movable block 106.

In the present disclosure, the driving end parts, the driven end parts and the clamping parts have two sets of left and right sides, their shapes and sizes are the same, and the functions are the same, but they work at different positions and timings. The device is used in the reciprocating propulsion mechanism and has two groups of clamping parts to clamp the guide wire. Under the cooperation of the camshaft 102 and gear transmission group 300 (the structure of the gear transmission group is shown in patent document 201911259494.4), two connecting rods in the gear transmission group are respectively connected with two sets of the main end connecting pieces to drive two sets of driving end parts to slide along the length of rectangular bottom plate, and then complete the clamping and propulsion with the clamping parts of the driven end parts. Four cams are provided on the camshaft, and the cams have a certain angle difference to ensure that at the same time, only one group of cams pushes the driving end part to make the guide wire clamper to clamp the guide wire 101. Therefore, only when the guide wire is clamped, the tactile force feedback device (the high precision weighing sensor) can collect the signal, and when the guide wire is loosened, it does not need to collect the signal of the sensor. The passive movable block 105 at the driven end of the propulsion mechanism is used to assist in tightening the guide wire. The polytetrafluoro patch 208 is adhered to the right-angle connecting plate 205. Under the action of the spring, the polytetrafluoro patch 208 always fits with the camshaft 102. When a group of active movable blocks 106 and passive movable blocks 105 clamp the guide wire 101, and the first electromagnet receives the force in the clamping direction of the guide wire, the force is transmitted to the right-angle connecting plate 205 through the U-shaped slot connector 201, the first slider 203 and the first micro linear guide 204. The high precision load cell 202 only measures the force along the axial direction of the guide wire, that is, the friction on the guide wire.

The disclosure provides a guide wire friction feedback method for interventional surgical robot, including:
using the guide wire friction feedback device for interventional surgical robot in conjunction with a reciprocating motion device of the interventional surgery robot;
clamping alternately and moving, by two sets of the clamping parts, the guide wire during the reciprocating motion of the guide wire;
measuring the friction force in a motion of the guide wire by detecting a force change signal from the high precision load cell to indirectly reflect the force on a guide wire end; and
transmitting a data to a control end of driving end of the robot propulsion mechanism to give timely feedback to a doctor.

In the disclosure, the precision of the high precision load cell is less than or equal to 0.01N.

In the description of the present specification, reference to the description of the terms "one embodiment", "some embodiments", "an example", "a specific example", or "some examples" or the like, is intended to refer to specific features, structures, materials or features that are included in at least one embodiment or example of the disclosure. In the specification, the schematic representations of the above terms are not necessarily directed to the same embodiments or examples. Moreover, the particular features, structures, materials, or features described may be combined in any one or more embodiments or examples in a suitable manner. In addition, those skilled in the art may join and combine the different embodiments or examples described in this specification.

Although the embodiments of the present disclosure have been shown and described above, it is to be understood that the embodiments described above are exemplary and not to be construed as limiting the disclosure. Variations, modifications, substitutions, and variations of the above-described embodiments may be made by one of ordinary skill in the art within the scope of the present disclosure.

What is claimed is:

1. A guide wire friction feedback device for an interventional surgical robot, comprising two sets of driving end parts, two sets of driven end parts, a first clamping part, and a second clamping part symmetrically arranged along a guide wire;
wherein each set of the driving end parts comprises a U-shaped slot connector, a high precision load cell, a first slider, a first micro linear guide, a right-angle connecting plate and a driving end connecting piece; a top of the driving end connecting piece slides along a direction parallel to the guide wire on a length direction of a rectangular bottom plate driving the driving end parts; a bottom of the right-angle connecting plate slides perpendicularly to the direction of parallel to the guide wire on the top of the driving end connecting piece; an outside of a vertical plate connected on one end of the right-angle connecting plate is butted with a camshaft, and a top of the other end of the right-angle connecting plate is fixed with the first micro linear guide parallel to the direction of the guide wire; the first slider slides on the first micro linear guide, and the U-shaped slot connector is fixed on a top of the first slider to counteract a clamping force of the guide wire; the high precision load cell is arranged perpendicularly to the guide wire; one end of the high precision load cell is fixed on an inner side of the vertical plate, and the other end of the high precision load cell is inserted into a notch of the U-shaped slot connector, and a width of the notch is greater than a width of the high precision load cell; the high precision load cell is used to measure a friction on the guide wire; a side far away from the notch of the U-shaped slot connector is fixed with one end of a first clamping part;
each set of the driven end parts comprises the second clamping part arranged corresponding to the first clamping part, and a driven end connecting piece arranged corresponding to the driving end connecting piece, for clamping and pushing the guide wire;
wherein each set of the driven end parts further comprises a third slider a driven end connecting plate, and a third micro linear guide; the driven end connecting plate is arranged opposite to the right-angle connecting plate; the driven end connecting piece is fixed near a side of the guide wire on the driven end connecting plate; a top of the driven end connecting plate is fixed with the third micro linear guide in parallel with the guide wire; the second clamping part is fixed on a top of the third slider and slides on the third micro linear guide;
wherein the first clamping part comprises a first cylindrical electromagnet and an active movable block; an axis of the first cylindrical electromagnet is perpendicular to the direction of the guide wire, and one end of the first cylindrical electromagnet is fixed on the U-shaped slot connector, and the other end of the first cylindrical electromagnet is magnetically connected with the active movable block;
wherein the second clamping part comprises a second cylindrical electromagnet and a passive movable block; the second cylindrical electromagnet is vertically fixed on the top of the third slider; a plane of an axis of the second cylindrical electromagnet is parallel to a plane of the guide wire, and a top of the second cylindrical electromagnet is magnetically connected with the passive movable block rubbing with the active movable block.

2. The guide wire friction feedback device of claim 1, wherein each set of the driving end parts further comprises a second slider and a second micro linear guide; the bottom of the right-angle connecting plate is fixed with the second slider along a vertical direction with the guide wire, and the top of the driving end connecting piece is provided with the second micro linear guide sliding with the second slider.

3. The guide wire friction feedback device of claim 1, wherein each set of the driving end parts further comprises a polytetrafluoro patch; and the polytetrafluoro patch is always butted with the camshaft.

4. A guide wire friction feedback method for an interventional surgical robot, comprising using the guide wire friction feedback device for the interventional surgical robot of claim 1 in conjunction with a reciprocating motion device of the interventional surgical robot;

clamping alternately and moving, by the first clamping part and the second clamping part, the guide wire during a reciprocating motion of the guide wire;

measuring a friction force in the reciprocating motion of the guide wire by detecting a force change signal from the high precision load cell to indirectly reflect a force on a guide wire end; and transmitting data based on the measured friction force to a control end of a driving end of a robot propulsion mechanism to give timely feedback to a doctor.

* * * * *